(12) United States Patent
Daniels et al.

(10) Patent No.: US 11,286,489 B2
(45) Date of Patent: Mar. 29, 2022

(54) POSH INHIBITOR COMPLEX BIOMOLECULES AND AMPHIPHILE MICELLES

(71) Applicants: Mark Daniels, Columbia, MO (US); Bret Ulery, Columbia, MO (US); David Porciani, Columbia, MO (US); Kwaku Tawiah, Columbia, MO (US); Josiah Smith, Columbia, MO (US); Leah Cardwell, Columbia, MO (US); Donald Burke, Columbia, MO (US); Erin Newcomer, Wildwood, MO (US)

(72) Inventors: Mark Daniels, Columbia, MO (US); Bret Ulery, Columbia, MO (US); David Porciani, Columbia, MO (US); Kwaku Tawiah, Columbia, MO (US); Josiah Smith, Columbia, MO (US); Leah Cardwell, Columbia, MO (US); Donald Burke, Columbia, MO (US); Erin Newcomer, Wildwood, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 337 days.

(21) Appl. No.: 16/076,521

(22) PCT Filed: Feb. 13, 2017

(86) PCT No.: PCT/US2017/017638
§ 371 (c)(1),
(2) Date: Aug. 8, 2018

(87) PCT Pub. No.: WO2017/139746
PCT Pub. Date: Aug. 17, 2017

(65) Prior Publication Data
US 2019/0040390 A1    Feb. 7, 2019

Related U.S. Application Data

(60) Provisional application No. 62/294,154, filed on Feb. 11, 2016.

(51) Int. Cl.
| | | |
|---|---|---|
| *A61K 38/00* | (2006.01) | |
| *C12N 15/115* | (2010.01) | |
| *A61K 38/10* | (2006.01) | |
| *A61K 9/107* | (2006.01) | |
| *A61P 35/00* | (2006.01) | |
| *A61K 38/16* | (2006.01) | |
| *C12N 9/00* | (2006.01) | |

(52) U.S. Cl.
CPC .......... *C12N 15/115* (2013.01); *A61K 9/1075* (2013.01); *A61K 38/10* (2013.01); *A61K 38/16* (2013.01); *A61P 35/00* (2018.01); *C12N 9/93* (2013.01)

(58) Field of Classification Search
CPC ...... A61K 38/16; A61K 38/10; A61K 9/1075; A61P 35/00; C12N 15/115; C12N 9/93
See application file for complete search history.

(56) References Cited

U.S. PATENT DOCUMENTS

| | | | |
|---|---|---|---|
| 8,338,366 B2 | 12/2012 | Lin et al. | |
| 8,828,928 B2 * | 9/2014 | Dittrich | ............... A61K 9/4825 514/3.2 |
| 9,901,617 B2 | 2/2018 | Daniels | |

FOREIGN PATENT DOCUMENTS

| | | | |
|---|---|---|---|
| WO | WO-2004078130 A2 * | 9/2004 | ........... A61K 31/122 |
| WO | WO 2006-066258 A2 | 6/2006 | |
| WO | WO 2015-023824 A2 | 2/2015 | |

OTHER PUBLICATIONS

Orava et al. Delivering cargoes into cancer cells using DNA aptamers targeting internalized surface portals. 2010. Biochimica et Biophysica Acta 1798 (2010) 2190-2200 (Year: 2010).*
Wei et al. SHROOM3-FYN Interaction Regulates Nephrin Phosphorylation and Affects Albuminuria in Allografts. 2018. J Am Soc Nephrol 29: 2641-2657, 2018. (Year: 2018).*
Takahashi, Masaki. Aptamers targeting cell surface proteins. 2017. Biochimie 145 (2018) 63-72 (Year: 2017).*
Chen et al. Fusion Protein Linkers: Property, Design and Functionality. 2013. Adv Drug Deliv Rev. Oct. 15, 2013; 65(10): 1357-1369. (Year: 2013).*
Karkkeainen et al. POSH2 is a RING finger E3 ligase with Rac1 binding activity through a partial CRIB domain. 2010. FEBS Letters 584 (2010) 3867-3872 (Year: 2010).*
Kärkkäinen et al. POSH2 is a RING finger E3 ligase with Rac1 binding activity through a partial CRIB domain. FEBS Letters 584 (2010) 3867-3872 (Year: 2010).*
Wei et al. SHROOM3-FYN Interaction Regulates Nephrin Phosphorylation and Affects Albuminuria in Allografts. J Am Soc Nephrol 29: 2641-2657, 2018 (Year: 2018).*
Takahashi et al. Aptamers targeting cell surface proteins. Biochimie 145 (2018) 63-72 (Year: 2018).*
Cunningham, C., et al., "The POSH/JIP-1 Scaffold Network Regulates TCR-Mediated JNK1 Signals and Effector Function in CD8+ T Cells", Eur. J. Immunol. 2013, vol. 43, pp. 3361-3371 (11 pgs).

(Continued)

*Primary Examiner* — Aradhana Sasan
*Assistant Examiner* — Mercy H Sabila
(74) *Attorney, Agent, or Firm* — Stinson LLP

(57) ABSTRACT

The present invention is directed to a composition that includes an amphiphile, its use in a method of preventing and/or treating cancer, and its use in a method of producing a pharmaceutical composition. In certain embodiments, the amphiphile includes a hydrophilic peptide that binds to a Plenty of SH3 domain (POSH) and inhibits or disrupts a POSH scaffold network, a hydrophobic moiety, and an aptamer. The present invention is also directed to other POSH inhibitor complex biomolecules that do not contain a hydrophobic moiety.

19 Claims, 2 Drawing Sheets

Specification includes a Sequence Listing.

(56) References Cited

OTHER PUBLICATIONS

Cui, H., et al., "Self-Assembly of Peptide Amphiphiles: From Molecules to Nanostructures to Biomaterials", Biopolymers. 2010; (4(1): 1-18. Doi:10.1002/bip.21328 (26 pgs).

Shen, D., et al., "Modulation of Nuclear Internalization of Tat Peptides by Fluorescent Dyes and Receptor-Avid Peptides", FEBS Lett. May 1, 2007; 581(9): 1793-1799 (16 pgs).

Lyons, T., et al., "Regulation of the Pro-Apoptotic Scaffolding Protein POSH by Akt", The Journal of Biological Chemistry, vol. 282, No. 30, pp. 21987-21997, Jul. 27, 2007 (12 pgs).

Rahmat, D., et al., "Synergistic Effects of Conjugating Cell Penetrating Peptides and Thiomers on Non-Viral Transfection Efficiency", Biomaterials 33 (2012) 2321-2326 (6 pgs).

International Search Report and Written Opinion dated May 11, 2017 issued in priority application PCT/US2017/017638 (15 pgs).

Orava, E.W. et al., "Delivering cargoes into cancer cells using DNA aptamers targeting internalized surface portals", Biochemica et Biophysica Acta, 2010, vol. 1798, pp. 2190-2200 (11 pgs).

Chen, X, et al., "Fusion protein linkers: property, design and functionality", Advanced Drug Delivery Reviews, 2013, vol. 65, pp. 1357-1369 (13 pgs).

Zhang, et al., "Converting Peptides into Drug Leads by Lipidation", Current Medicinal Chemistry, vol. 19, No. 11, 2012, pp. 1602-1618 (17 pgs).

Kovalainen, et al., "Novel Delivery Systems for Improving the Clinical Use of Peptides", Pharmacological Reviews, The American Society for Pharmacology and Experimental Therapeutics, Jul. 2015, pp. 541-561 (22 pgs).

Chung, et al., "In vivo biodistribution and clearance of peptide amphiphile micelles", Nanomedicine: Nanotechnology, Biology, and Medicine, vol. 11, 2015, pp. 479-487 (9 pgs).

Peters, et al., "Targeting atherosclerosis by using modular, multifunctional micelles", PNAS, vol. 106, No. 24, Jun. 16, 2009, pp. 9815-9819 (5 pgs).

\* cited by examiner

SEQUENCE LISTING

```
<160> NUMBER OF SEQ ID NOS: 4

<210> SEQ ID NO 1
<211> LENGTH: 20
<212> TYPE: PRT
<213> ORGANISM: Artificial Sequence
<220> FEATURE:
<223> OTHER INFORMATION: Synthetic

<400> SEQUENCE: 1

Glu Gly Lys Glu Pro Gly Asp Leu Lys Phe Ser Lys Gly Asp Ile Ile
1               5                   10                  15

Ile Leu Arg Arg
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Lys Glu Ala Asp Lys Asp Cys Leu Pro Phe Ala Lys Asp Asp Val Leu
1               5                   10                  15

Thr Val Ile Arg
            20
```

```
<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Arg Lys Glu Asp Glu Leu Glu Leu Arg Lys Gly Glu Met Phe Leu Val
1               5                   10                  15

Phe Glu Arg

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Pro Gln Ser Glu Ala Glu Leu Glu Leu Lys Glu Gly Asp Ile Val Phe
1               5                   10                  15

Val His Lys Lys
            20
```

POSH INHIBITOR COMPLEX BIOMOLECULES AND AMPHIPHILE MICELLES

CROSS-REFERENCE TO RELATED APPLICATIONS

This application is based on and claims priority to U.S. Provisional Application Ser. No. 62/294,154 filed on Feb. 11, 2016, which is hereby incorporated herein by reference.

INCORPORATION OF SEQUENCE LISTING

A computer readable form of the Sequence Listing containing the file named "0800528.0094_ST25.txt", which is 1,514 bytes in size (as measured in MICROSOFT OFFICE WINDOWS® EXPLORER), is provided herein and is herein incorporated by reference. This Sequence Listing consists of SEQ ID NOs:1-4.

BACKGROUND OF THE INVENTION

1. Field of the Invention

The present invention relates to anti-cancer therapeutics, more specifically, to a composition formed in part from a therapeutic biomolecule.

2. Description of Related Art

According to the World Health Organization over 500,000 people are diagnosed with lymphoma or leukemia each year. Unfortunately, despite numerous advances for some lymphoma and leukemia subtypes, high-risk patients (such as those diagnosed with early T cell precursor, B cell precursor, MLL or BCR/ABL-ALL) continue to be associated with a very poor prognosis.

Acute lymphoblastic leukemia (ALL) is a malignant cancer of lymphoid progenitor cells that can affect both children and adults. In the United States, more than 6,000 new cases of ALL are reported each year, two-thirds of which are children. In fact, it is the most common childhood cancer. While recent advancements in therapeutics have greatly increased the immediate and long-term survival associated with many cancers, ALL patients continue to have a poor prognostic outlook. Data from the American Cancer Society predicts that in the United States alone, nearly 25,000 people will die from leukemia next year. Current treatments for ALL include induction, intensification, and maintenance therapy in conjunction with central nervous system prophylaxis. While current therapies result in long term remission in more than 80% of pediatric patients, death from relapsed ALL is still the most frequent cause of death in children with cancer. Adult patients suffering with ALL have an even worse outcome with a 60-70% relapse rate within 5 years and a post-relapse median survival time of only 3-6 months. Recent ALL treatments utilizing monoclonal antibodies, bispecific antibodies, autologous natural killer cells, and chimeric antigen receptor T cells show significant potential. However, they have yet to receive widespread clinical implementation and have significant long-term side effects (such as lifelong immunodeficiency). Thus, there is a significant need for the development of new treatment modalities that are safer, more efficacious, and able to treat or circumvent drug-resistance directly.

Peptide drugs have emerged as a promising alternative cancer therapeutic. Recent clinical successes include the use of carfilzomib for the treatment of multiple myeloma and the use of cetrorelix for the treatment of hormone-sensitive prostate and breast cancers. The role different signaling pathways play in both healthy and aberrant lymphocyte development have recently been studied. The scaffold molecule Plenty of SH3 domains (POSH) had been previously described as a Rac-dependent, multi-functional c-Jun-N-terminal kinase (JNK) binding protein containing four highly conserved SH3 domains: (POSH SH3.1, POSH SH3.2, POSH SH3.3, and POSH SH3.4).

Peptides possess several drawbacks limiting their clinical translatability including low local peptide concentration (peptides are highly soluble), non-specific binding (peptides can induce significant off-target toxicity through delivery to healthy cells), limited internalization capacity, and susceptibility to enzymatic degradation such as enzymatic hydrolysis. This leads to low local peptide concentrations, which means that larger doses are required to be effective.

A variety of strategies have been implemented to counteract individual issues associated with peptide therapeutics including the addition of targeting moieties, cell penetrating peptides, and biomaterials-based drug carriers. Peptide amphiphiles are biomaterials comprised of peptide-hydrophobe conjugates that self-assemble into micelles in a medium (such as water) and have been shown capable of delivering biologically active peptides for a variety of applications including cancer therapy. The non-peptidic hydrophobe of peptide amphiphile micelles (PAMs) dictates their cellular internalization capacity. However, known amphiphiles that form PAMs suffer from drawbacks such as internalization by both all cells regardless of whether they are healthy or cancerous.

BRIEF SUMMARY OF THE INVENTION

In a first aspect, the present invention is directed to a composition that includes an amphiphile. The amphiphile includes a hydrophilic peptide and a hydrophobic moiety. The hydrophilic peptide binds to a Plenty of SH3 domain (POSH) and inhibits or disrupts a POSH scaffold network.

In certain embodiments, the composition includes an aptamer. Preferably, the aptamer has a specific binding affinity for a specific cell surface marker. Preferred specific cell surface markers are CD4, CD19, Transferrin Receptor, CD7, CD20, CD33, and CD13. Preferred aptamers include hCD4 and hCD19. Preferably, the hydrophobic moiety and aptamer are attached to opposite ends of the hydrophilic peptide, and each of the hydrophobic moiety and aptamer are independently attached via a compound such as cysteine, lysine, glutamic acid, aspartic acid, serine, threonine, tyrosine, maleimide, a modified cysteine, a modified lysine, a modified glutamic acid, a modified aspartic acid, a modified serine, a modified threonine, a modified tyrosine, or a modified maleimide.

In certain embodiments, the hydrophobic moiety includes an aliphatic compound. Preferably, the hydrophobic moiety includes a lipid comprising a saturated or unsaturated fatty acid. More preferably, the hydrophobic moiety is selected from the group comprising of palmitic acid, oleic acid, eicosapentaenoic acid, n-decylamine, oleylamine, or combinations and/or multiples thereof. Most preferably, the hydrophobic moiety is dipalmitoyllysyllysine (KKP2) or dipalmitoylglutamylsuccinate lysine (diC16 lysine-K (diC16)). In certain embodiments, the amphiphile includes two hydrophobic moieties.

In certain embodiments, the composition includes a plurality of amphiphiles and a medium in which at least a portion of the amphiphiles is insoluble, such that at least a portion of the plurality of the amphiphiles are arranged as micelles in the medium. Preferably, the medium is an aqueous medium. Preferably, the composition further comprises a biomolecule that includes a second aptamer and a second hydrophilic peptide that binds to a Plenty of SH3 domain (POSH) and inhibits or disrupts a POSH scaffold network, but does not include a hydrophobic moiety.

In certain embodiments, the hydrophilic peptide includes a sequence that is SEQ. ID. NO: 1 (EGKEPGDLKFSKGDIIILRR), SEQ. ID. NO: 2 (KEADKDCLPFAKDDVLTVIR), SEQ. ID. NO: 3 (RKEDELELRKGEMFLVFER), or SEQ. ID. NO: 4 (PQSEAELELKEGDIVFVHKK) and an amino acid sequence having over it total length at least 50% sequence identity with any one of SEQ. ID. NO: 1 to SEQ. ID. NO: 4.

In another aspect, the present invention is directed to a method of preventing and/or treating cancer. The method includes the step of administering the composition of the first aspect of the present invention to a subject. Preferably, the administering step includes administering the composition of the first aspect of the present invention to the subject at a dose suitable for inhibiting or disrupting POSH scaffold networks.

In yet another aspect, the present invention is directed to a method of producing a pharmaceutical composition. The method includes the steps of adding the composition of the first aspect of the present invention to an aqueous medium, wherein the aqueous medium is pharmaceutically acceptable, and allowing the amphiphile to arrange into micelles.

In still another aspect, the present invention is directed to a plurality of amphiphiles. Each amphiphile includes a hydrophobic moiety and (a) a hydrophilic peptide that binds to a Plenty of SHE domain (POSH) and inhibits or disrupts a POSH scaffold network, (b) an aptamer, or (c) combinations thereof. Preferably, the composition includes a medium in which at least a portion of said amphiphiles are insoluble and wherein said insoluble amphiphiles form micelles in said medium. Preferably, at least a portion of the micelles are heterogeneous. Preferably, the composition is heterogeneous.

In one more aspect, the present invention is directed to a composition that includes a hydrophilic peptide and an aptamer. The hydrophilic peptide binds to a Plenty of SH3 domain (POSH) and inhibits or disrupts a POSH scaffold network.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
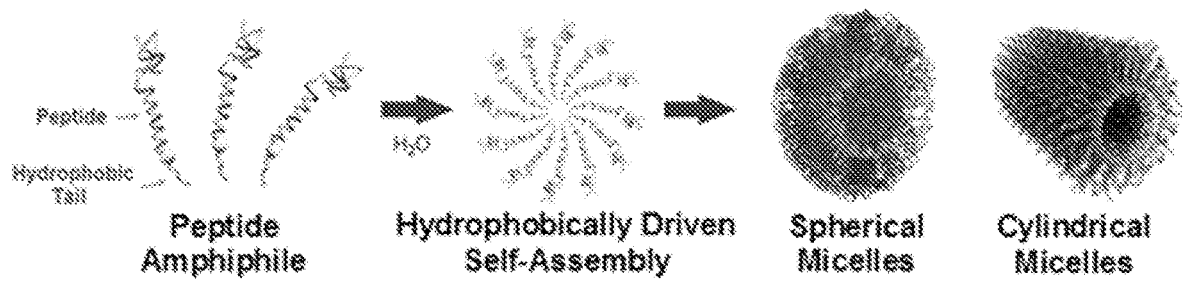
FIG. 1 depicts how peptide amphiphiles self-assemble into spherical and/or cylindrical micelles through hydrophobically driven interactions with an aqueous medium.

One aspect of the present invention is directed to a composition that includes one or more amphiphiles. As used herein, "amphiphiles" of the present invention include a hydrophobic moiety and a hydrophilic peptide and/or a hydrophilic aptamer. Amphiphiles that contain a hydrophilic peptide are sometimes referred to herein as peptide amphiphiles. The present invention is further directed to a composition in which a plurality of amphiphiles are arranged into micelles in a pharmaceutically acceptable medium, as well as methods of making and using such compositions. The present invention is further directed to POSH inhibitor complex biomolecules, compositions comprising a plurality of such biomolecules, as well as methods of making and using such compositions. When used herein a complex biomolecule of the present invention comprises a hydrophobic moiety, a hydrophilic peptide and/or a hydrophilic aptamer. The POSH inhibitor complex biomolecules include amphiphiles of the type described herein, as well as biomolecules comprising a POSH inhibitor peptide and an aptamer, but not containing a hydrophobic moiety.

In one preferred embodiment, the hydrophilic peptide binds to a POSH domain (e.g. SH3.1, POSH SH3.2, POSH SH3.3, or POSH SH3.4) and inhibits or disrupts a POSH scaffold network. Such peptides may be referred to as POSH inhibitor peptides. Exemplary POSH inhibitor peptides are disclosed in U.S. Pat. Pub. No. 2016/0193292, which is incorporated herein by reference. In certain embodiments, the hydrophilic peptide includes a sequence that is selected from SEQ. ID. NO: 1 (EGKEPGDLKFSKGDIIILRR), SEQ. ID. NO: 2 (KEADKDCLPFAKDDVLTVIR), SEQ. ID. NO: 3 (RKEDELELRKGEMFLVFER), SEQ. ID. NO: 4 (PQSEAELELKEGDIVFVHKK), and an amino acid sequence having over its total length at least 90%, 80%, 70%, 60% or 50% sequence identity with any one of SEQ. ID. NO: 1 to SEQ. ID. NO: 4.

In certain embodiments, the peptides are synthesized using modern Fmoc (Fluorenylmethyloxycarbonyl)-protected solid phase synthesis on-resin. Several orthogonal protection strategies have been used to allow for selective modification of peptide side-chains during synthesis. The peptides have been synthesized in one linear sequence or in several portions that are joined after cleavage from the resin, dependent on the specific sequence.

Recent research has revealed that POSH plays a crucial role in T and B cell differentiation and oncogenesis and peptide binding-based disruption of this region serves as a possible cancer target, including possibly targeting ALL. The inventors are aware of no other therapeutic peptides useful for the treatment of ALL. POSH inhibition does not have an effect on normal lymphocyte homeostasis. Using a cell permeable peptide mimic of POSH SH3.3 known as TAT-POSH—where TAT is an HIV regulatory protein capable of facilitating intracellular payload delivery—it was determined that the cell type and differentiation state of the T cell dictated the functions regulated by this scaffold molecule. Interestingly, recent experiments showed that while exposure to TAT-POSH has no effect on the survival or differentiation of healthy T and B cells, an overwhelming majority of precursor T and B cell leukemias tested (15 of 16) succumbed to POSH disruption. These data suggest that the untimely acquisition of the POSH function is a common event in lymphocyte oncogenesis making it a valuable target for novel broad-spectrum leukemia therapies.

Previous attempts to improve the efficacy of the POSH inhibitor peptide have focused on the use of cell-penetrating peptides like TAT-POSH, as described in U.S. Pat. Pub. No. 2016/0193292. Although TAT-POSH has been shown to improve POSH inhibitor effectiveness, it is still associated with the drawbacks outlined above in the background section, including lack of cell specific targeting.

The hydrophobic moiety of the amphiphiles of the present invention may comprise an aliphatic moiety. The hydrophobic moiety may include a lipid, including saturated or unsaturated fatty acids, composed of hydrocarbons with one or more reactive centers, such as carboxylic acid, amine, alcohol, thiol, or maleimide, capable of conjugation to a peptide. Suitable hydrophobic moieties include, but are not limited to, palmitic acid, oleic acid, eicosapentaenoic acid, n-decylamine, and oleylamine, or combinations these hydrophobic moieties, created through standard synthetic organic chemistry techniques. Combinations of hydrophobic moieties may include multiples of a hydrophobic moiety, for example dipalmitoylyslysine (KKP2). In certain embodiments, amphiphiles of the present invention may include only one hydrophobic moiety, two hydrophobic moieties, or more than two hydrophobic moieties. Certain embodiments include up to eight hydrophobic moieties.

The hydrophobic moiety is preferably joined to the hydrophilic peptide via a covalent bond. The hydrophobic moiety may be attached to either the C-terminus or the N-terminus of the peptide via any suitable linkage. If multiple hydrophobic moieties are present, some may be attached to the C-terminus, while others may be attached to the N-terminus, or all hydrophobic moieties may be attached to the same end of the peptide. Suitable linkages may comprise a compound selected from the group consisting cysteine, lysine, glutamic acid, aspartic acid, serine, threonine, tyrosine, maleimide, a modified cysteine, a modified lysine, a modified glutamic acid, a modified aspartic acid, a modified serine, a modified threonine, a modified tyrosine, or a modified maleimide. In such embodiments, suitable hydrophobic moieties include, but are not limited to, dipalmitoyllysyllysine (KKP2) and dipalmitoylglutamylsuccinatelysine (diC$_{16}$ lysine-K (diC$_{16}$)). In certain embodiments, one or more hydrophobic moieties may be attached to an aptamer, as discussed in more detail below.

In certain embodiments, amphiphiles are made by conjugating a lipid to the peptide. Dependent on the lipid and peptide chosen, one example of a synthetic route is to join the lipid to the peptide using a thiol-maleimide click reaction. After synthesis is complete, the products may be purified via reverse phase high-pressure liquid chromatography.

The amphiphiles of the present invention may include one or more aptamers. Aptamers are a type of targeting moiety that are structured nucleic acids that recognize specific molecular binding partners and can be utilized to target receptors on desired cell populations. They are developed through a process termed selective evolution of ligands by exponential enrichment (SELEX) which allows for their binding specificity, internalization potential, and nuclease resistance to be simultaneously designed for during their development. These molecules have been adapted to enhance the tumor cell killing of peptide-based therapeutics. However, the inclusion of an aptamer targeting moiety to the TAT-POSH peptide causes the peptide to have a highly negatively charged aptamer phosphodiester backbone that can complex with the significant positive charge of the TAT sequence, which can impede each component's individual effects.

In certain embodiments, the aptamer is joined to either a hydrophobic moiety, or to a hydrophilic peptide that is joined to a hydrophobic moiety. The aptamer preferably is joined to the hydrophilic peptide or hydrophobic moiety by a covalent bond. The aptamer may extend from either the C-terminus or the N-terminus of the hydrophilic peptide, on the end opposite to which the hydrophobic moiety is linked, via any suitable linkage. If the hydrophobic moiety is attached to the C-terminus, then the aptamer will be attached to the N-terminus, and vice-versa. If multiple aptamers are present, they will likely be attached to the same end of the peptide with the same linkage, although they could be attached at other reactive centers within the peptide. Suitable linkages may comprise a compound selected from the group consisting of cysteine, lysine, glutamic acid, aspartic acid, serine, threonine, tyrosine, maleimide, a modified cysteine, a modified lysine, a modified glutamic acid, a modified aspartic acid, a modified serine, a modified threonine, a modified tyrosine, or a modified maleimide. Thioester modified aptamers may also be used. Attachment of the aptamer can also be accomplished via a thiol-maleimide click reaction or via association of the aptamer to a complementary DNA or RNA sequence covalently linked to the peptide or binding peptide region. In embodiments wherein an aptamer is linked to a hydrophobic moiety without an intervening hydrophilic peptide, the aptamer is joined to the hydrophobic moiety via a covalent bond or via a complementary RNA or DNA sequence, as discussed above.

The aptamers facilitate directed delivery of the amphiphile or other complex biomolecules to cellular sub-populations. In other words, the aptamers enhance the directed delivery of the amphiphile or other complex biomolecules to highly specific cells, thus enhancing the amphiphile or other complex biomolecule's overall performance while limiting its undesirable off-target effects. Suitable aptamers are formed from RNA, DNA, 2'-modified RNA, and nucleic acids with additional covalent modifications such as peptide or protein side chains. Aptamers can yield binding partner association orders of magnitude tighter and more specific than other targeting moieties such as antibodies and proteins.

In certain embodiments, the aptamers have a specific binding affinity for a specific cell surface marker expressed by a certain type of cell, for example specific cell surface markers expressed by lymphocytes, specific cell surface markers expressed by specific types of lymphocytes and/or specific cell surface markers expressed by a tumor. Exemplary specific cell surface markers include, but are not limited to, CD4, CD19, Transferrin Receptor, CD7, CD20, CD33, and CD13. Suitable aptamers include, but are not limited to, human CD4 (hCD4) or human CD19 (hCD19). The targeted cells expected to be affected are outlined in Table 1. In certain embodiments, where an aptamer is hCD4 or hCD19, the hydrophobic moiety of the amphiphile may be dipalmitoyllysyllysine (KKP2) or diC$_{16}$ lysine (K(diC$_{16}$)).

TABLE 1

| Aptamer | | | Targeted Cell Lines | | Positive Outcomes | |
|---|---|---|---|---|---|---|
| Name | Target | Specificity | Positive | Negative | Internalization | Function |
| hCD4 | CD4 | human | MOTN1 | MEC1 | ONLY MOTN1 | ONLY MOTN1 dies |
| hCD19 | CD19 | human | MEC1 | MOTN1 | ONLY MEC1 | ONLY MEC1 dies |

While such aptamers do not specifically target only tumors, POSH inhibition does not have an effect on normal lymphocyte homeostasis. Thus, the effect of POSH inhibition in the aptamer targeted cell type is tumor specific. This limits the number of cells that are inhibited and decreases the possibility off target toxicity. In certain embodiments, tumor specific aptamers that will bind to specific cell surface markers only expressed on tumor cells may be generated.

The present invention is also directed to POSH inhibitor complex biomolecules, which may include any of the amphiphiles described herein, as well as biomolecules comprising a POSH inhibitor peptide and an aptamer, but not containing a hydrophobic moiety. The POSH inhibitor peptide may be any of the POSH inhibitor peptides described herein, and the aptamer may be any of the aptamers described herein. The POSH inhibitor peptide may be joined to the aptamer by any of the linkages and methods described herein with respect to joining aptamers to peptides.

In certain embodiments, the composition of the present invention includes a plurality of amphiphiles of the present invention and a pharmaceutically acceptable medium. Preferably the medium is one in which the hydrophobic moiety of a given amphiphile is insoluble, such that the amphiphiles arrange into micelles in the medium. Suitable media include, but are not limited to, an aqueous medium, such as water, or other pharmaceutically acceptable media in which the hydrophobic moieties of the amphiphiles being utilized are insoluble and will from micelles. The present invention also includes compositions comprising a plurality of the POSH inhibitor complex biomolecules of the present invention that comprise POSH inhibitor peptide joined to aptamers but not a hydrophobic moiety, and pharmaceutically active medium. Such biomolecules will not self-assemble into micelles. However, compositions comprising such biomolecules may also comprise a plurality of amphiphiles and micelles, in any of the types and combinations described herein.

Micelles comprising the amphiphiles of the present invention will form in such media through hydrophobically-driven self-assembly where the hydrophobic component is shielded from the aqueous environment by the hydrophilic component. See FIG. 1. In other words, amphiphiles self-assemble into micelles in an aqueous medium by hiding their hydrophobes within the micelle core (i.e., the interior of the sphere or cylinder) and displaying their hydrophilic peptides on the micelle corona (i.e., the exterior of the sphere or cylinder), for which the corona is water stable. Unlike most previously known amphiphiles, the amphiphiles of the present invention readily form micelles in an aqueous medium at very low concentrations, and this is due to the fact that the hydrophilic peptide (and aptamers, where included) are extremely hydrophilic.

It was surprisingly found that amphiphiles of the present invention comprising an aptamer, hydrophilic peptide and hydrophobic moiety can form spherical micelles, and this is also due to the fact that the hydrophilic peptide (and aptamers, where included) are extremely hydrophilic. Many other known amphiphilic peptides, including amphiphilic peptides comprising $diC_{16}$, form only or primarily cylindrical micelles. The contrast between spherical and cylindrical micelles, generally, is shown in FIG. 1. The spherical micelles formed from the amphiphiles of the present invention are advantageous in that they are better able to target specific tissues. The spherical nature of the amphiphiles can be enhanced by adding non-native peptide like sequences as a linker between the peptide and hydrophobic moiety to favor spherical micelle formation. The micelles are preferably sufficiently small to allow intravenous (IV) administration.

Micelles can trap a large number (hundreds to tens of thousands) of the amphiphiles together, which greatly increases the local concentration of the peptide when the micelles interact with the target cells. This allows for: a high local payload concentration, disassembly upon cell contact followed by lipid bi-layer intercalation facilitating cytosolic delivery, and payload protection from enzymatic degradation. Upon interaction with the targeted cells, the micelles are not internalized by the cells as whole nanoparticles, and instead disassemble and interact with cell lipid bi-layers.

Aptamers may be incorporated into micelles via multiple routes. In certain embodiments, aptamer amphiphiles are made via the conjugation of a lipid to an aptamer and co-dissolved with the peptide amphiphiles in a solvent, such as methanol. After methanol evaporation, the resulting film is dissolved in water or other water-based solvent, forming heterogeneous micelles. An alternative route to incorporating aptamers onto micelles include attaching the aptamer to the peptide of a peptide amphiphile during peptide synthesis or after micelle formation. This can be accomplished via many strategies, including a thiol-maleimide click reaction or association of the aptamer to a complementary DNA or RNA sequence covalently linked to the peptide or binding peptide region.

The incorporation of aptamers, including any of the aptamers described above, can allow for the directed delivery of the micelles to cancerous lymphocytes presenting highly specific surface markers. This is a benefit over prior art micelles that do not have the capacity to target desired cell populations. More specifically, where aptamers are included in the amphiphiles of a given micelle, the aptamers are displayed on the exterior of the micelle (the micelles allow for aptamer multimerization on their surface), and this enhances the interaction of each amphiphile that is joined with an aptamer with a desired cell population. The cancer cytotoxicity of these aptamer-containing micelles can be synergistically enhanced through the entrapment of classical small molecular chemotherapeutics like doxorubicin, or the entrapment of other adjuvants, in the hydrophobic micelle core. The fact that the aptamers are adhered to the amphiphiles via covalent tethering makes the micelles of the present invention superior to other previously known amphiphile micelles in which aptamers were incorporated through encapsulation or heterogeneous self-assembly, but not through covalent tethering directly to an amphiphile. Covalently tethering aptamers to amphiphiles is superior to encapsulation or heterogeneous self-assembly because the aptamers cannot be lost from the amphiphiles, which results in higher cell specificity, administration of higher doses and prevention of leakage.

The modularity of the amphiphiles allows for the design of heterogeneous micelles and heterogeneous combinations of micelles in the compositions, with the capacity to display multiple aptamers, deliver multiple peptides, and entrap multiple hydrophobic moieties at a variety of ratios. This flexibility allows for tailoring amphiphiles, micelles and compositions for the treatment of a variety of leukemia and lymphoma types, patient specific treatments, and treatment of other difficult to treat cancers. For example, an individual amphiphile can contain (a) one, two or more peptide sequences (including any of the peptides described above), each of which may be the same or different, (b) one, two, or more aptamers (including any of the aptamers described above), each of which may be the same or different and (c) one, two or more hydrophobic moieties (including any of the hydrophobic moieties described above), each of which may be the same or different. Similarly, the amphiphiles that make up an individual micelle may all be the same or may be different in composition, including different combinations of peptides, aptamers, and/or hydrophobic moieties. For example, amphiphiles that independently contain two different peptides known to work together (e.g. a SH3.3 inhibitor and a SH3.4 inhibitor) can be combined in a single micelle. The composition itself can also contain micelles that may all be the same composition or may be different, where individual micelles may themselves be internally homogenous or heterogeneous, in any of the combination described above. In addition, heterogeneous micelles and compositions can be prepared that include one or more of the following: 1) amphiphiles that comprise hydrophobic moieties and hydrophilic peptides but no aptamers are included; 2) amphiphiles that comprise hydrophobic moieties, hydrophilic peptides, and aptamers; and 3) amphiphiles that comprise hydrophobic moieties joined directly to aptamers but no hydrophilic peptides are included. However, when amphiphiles with no hydrophilic peptides are employed, they are combined with amphiphiles that do contain hydrophilic peptides, either combined within individual micelles, or contained in other micelles within the composition.

The present invention is also directed to a method of preventing and/or treating cancer. The method includes the step of administering any of the compositions of the invention to an individual. The small size of the micelles of the present invention allows intravenous administration, although other methods of administration known in the art may be used. The individual may be a human or a non-human animal. The amphiphiles of the compositions of the present invention may also be used to treat a variety of leukemias and other cancers, including but not limited to lymphoma, colon, breast, liver, prostate, lung, and melanoma cancers.

The present invention is also directed to methods of producing a pharmaceutical composition comprising the amphiphiles of the present invention. The method may include the steps of adding amphiphiles of the invention to a pharmaceutically acceptable medium in which the amphiphiles are insoluble, and allowing the amphiphiles to arrange into micelles. Suitable media include, but are not limited to water, or any water-based solvent. In certain embodiments, amphiphiles are dissolved in a co-solvent, such as methanol, in which the amphiphiles are soluble. The solvent is dried by evaporation. The resulting film is then added to a medium in which the amphiphile is not soluble to form micelles. To form compositions that comprise POSH inhibitor complex biomolecules of the present invention that include biomolecules comprising POSH inhibitor peptides joined to aptamers (but not to hydrophobic moieties), such biomolecules may be added to a composition comprising any of the combinations of amphiphiles and micelles described herein.

Homogenous micelles may be formed by using only one type of amphiphile. Heterogeneous micelles may be formed by combining amphiphiles with desired components in the desired ratios. For example, amphiphiles independently comprising different peptides can be combined in a micelle. Homogenous compositions may be formed by using only one type of micelle. Heterogeneous compositions may be formed by using micelles with desired amphiphile components in the desired ratios. The desired ratios may depend on the target cell and/or the peptide cargo.

The amphiphiles, micelles, and compositions of the present invention produce a cell specific delivery system that targets specific cell population and affects only cancer cells. In certain embodiments, the amphiphiles of the present invention show highly specific cytotoxicity in a variety of T cell and B cell cancers and can be used to treat leukemia and lymphoma. Importantly, it has been surprisingly found that amphiphiles of the composition of the present invention are more effective than TAT-POSH, even when administered at a comparatively lower dose, as discussed in Example 1, below. The combination effects of adding aptamers and a hydrophobic tail to the therapeutic peptide is expected to result in enhanced and synergistic benefits over known therapeutic peptide delivery systems. The modularity of the amphiphiles allows the amphiphiles, micelles and compositions to be designed to target a specific cancers or cancer cells and to combine therapeutic peptides in a single micelle or composition. The ability to create amphiphiles that independently comprise a hydrophobic tail with an aptamer and/or therapeutic peptide to produce three types of molecules is also beneficial in tailoring the composition for the intended use. It was also surprisingly found that amphiphiles of the present invention are more effective at a lower dose than other therapeutic peptide constructs.

Certain aspects of the present invention are illustrated by the following non-limiting examples.

Example 1

POSH, TAT-POSH, and POSH-KKP2 Synthesis

POSH and TAT-POSH peptides were synthesized by Fmoc solid phase synthesis and purified by high pressure liquid chromatography. An ε-lysyllysine residue was added to the C-terminus of POSH through which two hydrophobic aliphatic palmitic acid moieties were conjugated, yielding the amphiphile POSH-KKP$_2$.

Micelle Formation and Characterization

Figure 2:
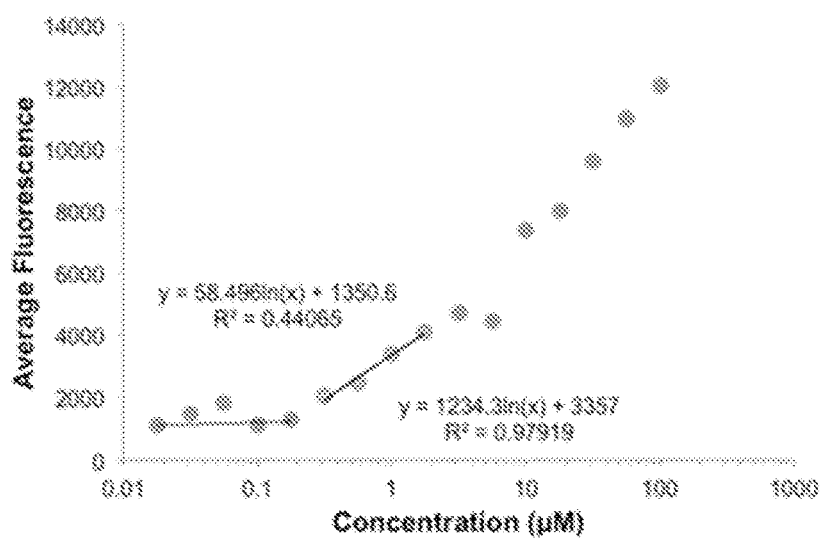
FIG. 2 depicts a graph that shows the average fluorescence of 1,6-diphenyl-1,3,5-hexatriene incubated with POSH-KKP2 at varying concentrations.

POSH-KKP2 was solubilized in water and micelle formation and morphology were assessed by previously established characterization techniques. The capacity for POSH-KKP2 to self-assemble into micelles was evaluated by a critical micelle concentration (CMC) assay where 1,6-diphenylthexatriene greatly increases in fluorescence intensity when trapped within the micelle core. POSH-KKP$_2$ amphiphiles readily formed micelles as indicated by a very low CMC of 0.18 µM as shown in FIG. 2.

Figure 3:
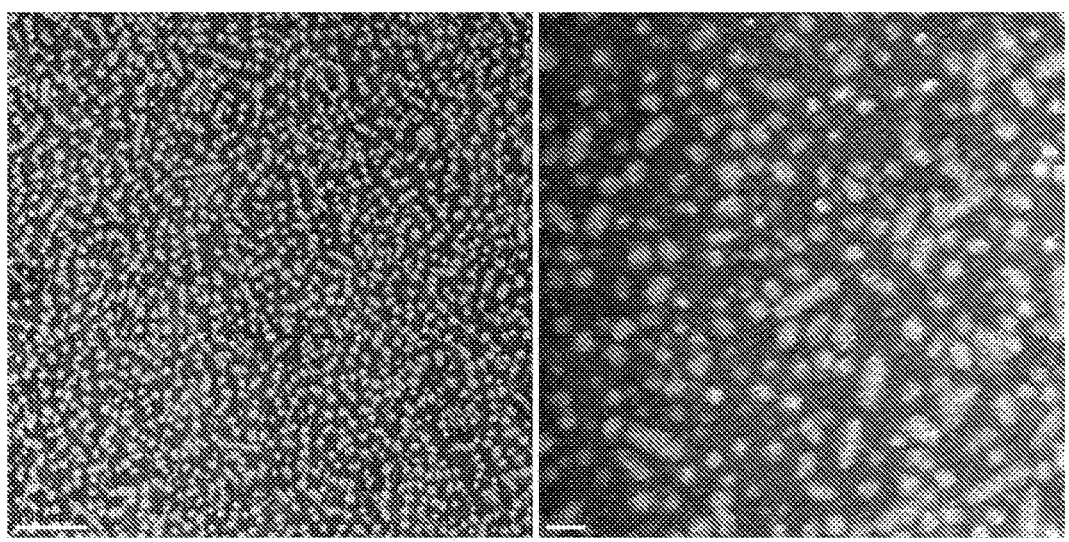
FIG. 3 depicts a transmission electron microscopy images of POSH-KKP2 self-assembled micelles with scale bars of 100 um (left panel) and 20 um (right panel).
Figure 4:
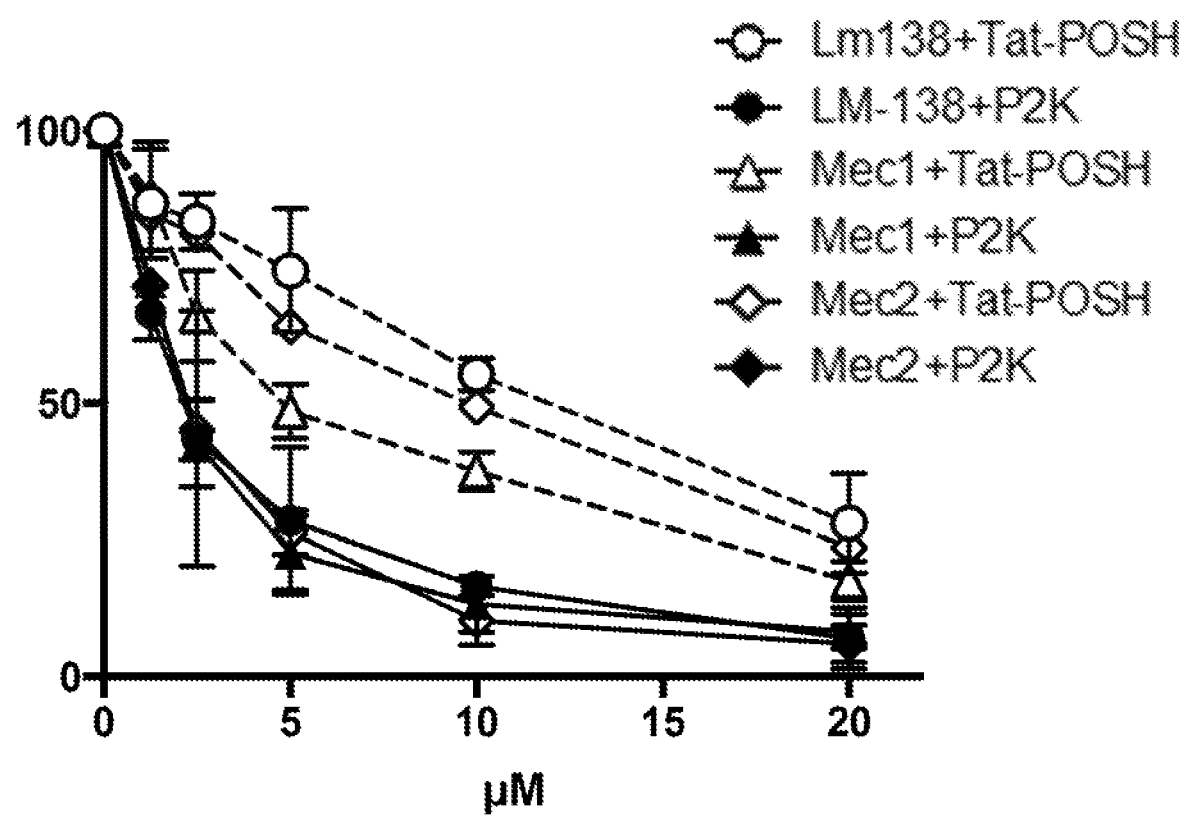
FIG. 4 depicts a graph that shows the percentage of different leukemic cells (LM-139, Mec-1, and Mec-2) that remain alive after exposure to a variety of doses of both TAT-POSH and POSH-KKP2.

Transition electron microscopy (TEM) revealed that POSH-KKP$_2$ self-assembled into micelles (FIG. 3) of which most were spheres (diameter—9.7±1.9 nm) though some were short cylinders (length—21.0±6.2 nm). As shown in FIG. 3, POSH-KKP2 amphiphile solutions (20 µM) were incubated on copper grids and the solution rapidly wicked away. Grids were negatively stained with an aqueous Nano-Tungsten solution and then observed using a transmission electron microscope (TEM). Micrographs were taken at 15,000× (left) and 45,000× (right) magnification and have scale bars of 100 nm and 20 nm, respectively, which showed the presence of mostly spherical micelles and some short cylindrical micelles. TAT-POSH and POSH-KKP$_2$ were incubated at 37° C. for 24 hours with different leukemic cells (LM-138, Mec-1, and Mec-2) at a variety of doses (1.25, 2.5, 5, 10, and 20 μM) after which therapeutic cytotoxicity was evaluated by flow cytometry. The results are shown in FIG. 4.

Results

When leukemic cells (LM-138) were exposed to TAT-POSH or POSH-KKP$_2$, dose dependent cytotoxicity was observed for both products (FIG. 4) though POSH-KKP$_2$ outperformed TAT-POSH at every dose. LM138 mouse proB leukemic cells transduced to overexpress BCR-ABL were cultured and 10$^6$ cells were incubated with varying concentrations of TAT-POSH or POSH-KKP$_2$ micelles at 37° C. for 24 hours. Cell death was assessed by flow cytometry and experimental groups were standardized against cells exposed to no stimulus (Control).

The capacity for POSH-KKP$_2$ micelles to enhance cytotoxicity over a gold-standard intracellular delivery system like TAT-POSH is an exciting and surprising discovery. Even more remarkable is that POSH-KKP$_2$ micelles induced similar cell death (~37% v. ~39%) at a sixteenth of the dose of TAT-POSH (1.5 μM v. 2.0 μM). Additionally, the highly hydrophilic and charged nature of the POSH peptide facilitated the formation of small POSH-KKP$_2$ micelles which will allow for their future intravenous delivery and in vivo evaluation.

Example 2

The results of Example 1 are consistent with results generated with human B cell leukemia Mec-1 and Mec-2 cells as discussed herein. When peptide amphiphiles comprised of hydrophilic CD19-aptamer-Tat-POSH peptide and a hydrophobic moiety were exposed to water they self-assembled into spherical or cylindrical micelles by hiding their hydrophobic moieties in their core and displaying their hydrophilic aptamer-peptides on their surface. As shown in FIG. 3, an electron micrograph of the POSH-KKP2 micelles confirmed their spherical shape. 2× serial dilutions of POSH-KKP2 micelles (20 μM starting concentration) were incubated with murine Bcr/Abl+ BCP-ALL LM138, Human B-CLL Mec1 and Mec2 cells for 24 hours in vitro. Percent survival was measured by flow cytometry (7AAD, active caspase-3). Curves (n=3 for each) were analyzed by non-linear regression. F test analyses of Tat-POSH vs. of POSH-KKP$_2$. $p<0.001$ (Prism by GraphPad). The results are shown in FIG. 4 (P2K means POSH-KKP2).

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

---

We claim:

1. A composition comprising:
    a plurality of amphiphiles comprising:
        a hydrophilic therapeutic peptide that inhibits or disrupts a scaffold network of POSH by targeting an SH3 domain of POSH selected from the group consisting of POSH SH3.1, POSH SH3.2, POSH SH3.3, and POSH SH3.4; and
        a hydrophobic moiety; and
    a medium in which at least a portion of the hydrophobic moieties of the amphiphiles is insoluble, such that at least a portion of the plurality of said amphiphiles are arranged as micelles in the medium.

2. The composition of claim 1, wherein the amphiphile further comprises an aptamer.

3. The composition of claim 2, wherein the aptamer has a specific binding affinity for a specific cell surface marker.

4. The composition of claim 3, wherein the aptamer has a specific binding affinity for a specific cell surface marker selected from the group consisting of CD4, CD19, Transferrin Receptor, CD7, CD20, CD33, and CD13.

5. The composition of claim 1, wherein the hydrophobic moiety comprises an aliphatic compound.

6. The composition of claim 5, wherein the hydrophobic moiety comprises a lipid comprising a saturated or unsaturated fatty acid.

7. The composition of claim 6, where the hydrophobic moiety is selected from the group consisting of palmitic acid, oleic acid, eicosapentaenoic acid, n-decylamine, oleylamine, and combinations thereof.

8. The composition of any of claim 1, wherein the amphiphile comprises two hydrophobic moieties.

9. The composition of claim 2, wherein the hydrophobic moiety and aptamer are attached to opposite ends of the hydrophilic peptide, and each of the hydrophobic moiety and aptamer are independently attached via a compound selected from the group consisting of cysteine, lysine, glutamic acid, aspartic acid, serine, threonine, tyrosine, maleimide, a modified cysteine, a modified lysine, a modified glutamic acid, a modified aspartic acid, a modified serine, a modified threonine, a modified tyrosine, or a modified maleimide.

10. The composition of claim 7, wherein the hydrophobic moiety is selected from the group consisting of dipalmitoyl-lysyllysine (KKP2) and dipalmitoylglutamylsuccinate lysine (diC16 lysine-K(diC16)).

11. The composition of claim 1, wherein the medium is an aqueous medium.

12. The composition of claim 11, wherein the composition further comprises a biomolecule comprising:
    a second hydrophilic peptide that inhibits or disrupts a scaffold network of POSH by targeting an SH3 domain of POSH selected from the group consisting of POSH SH3.1, POSH SH3.2, POSH SH3.3, and POSH SH3.4; and
    a second aptamer;
    wherein the biomolecule does not comprise a hydrophobic moiety.

13. The composition of claim 1, wherein the micelles are spherical.

14. The composition of claim 2, wherein the aptamer is selected from the group consisting of human CD4 (hCD4) and human CD19 (hCD19).

15. The composition of any of claim 1 or 14, wherein the hydrophilic peptide comprises a sequence selected from the group consisting of: SEQ. ID. NO: 1 (EGKEPGDLKFSKGDIILRR), SEQ. ID. NO: 2 (KEADKDCLPFAKDDVLTVIR), SEQ. ID. NO: 3 (RKEDELELRKGEMFLVFER), SEQ. ID. NO: 4 (PQSEAELELKEGDIVFVHKK) and an amino acid sequence having over it total length at least 50% sequence identity with any one of SEQ. ID. NO: 1 to SEQ. ID. NO: 4.

16. A composition comprising:
    a plurality of amphiphiles, each amphiphile independently comprising:

a hydrophobic moiety; and
(a) hydrophilic peptide that and inhibits or disrupts a scaffold network of POSH by targeting an SH3 domain of POSH selected from the group consisting of POSH SH3.1, POSH SH3.2, POSH SH3.3, and POSH SH3.4, (b) an aptamer, or (c) combinations thereof;

wherein at least a portion of said amphiphiles comprise said hydrophilic peptide; and a medium in which at least a portion of the hydrophobic moieties of the amphiphiles is insoluble, such that at least a portion of the plurality of said amphiphiles are arranged as micelles in the medium.

17. The composition of claim 16, wherein at least a portion of said micelles are heterogeneous.

18. The composition of claim 16, wherein the composition is heterogeneous.

19. The composition of claim 16, wherein the micelles are spherical.

\* \* \* \* \*